United States Patent
Adam et al.

(10) Patent No.: US 12,054,451 B1
(45) Date of Patent: Aug. 6, 2024

(54) WATER SOLUBLE PLATINUM (II) AMINO ACID SCHIFF BASE AS AN ANTITUMOR DRUG

(71) Applicant: KING FAISAL UNIVERSITY, Al-Ahsa (SA)

(72) Inventors: Mohamed Shaker Sayed Adam, Al-Ahsa (SA); Obadah S. Abdel-Rahman, Al-Ahsa (SA); Ahmed Desoky M. Mohamed, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/402,996

(22) Filed: Jan. 3, 2024

(51) Int. Cl.
*A61P 35/00* (2006.01)
*C07C 309/29* (2006.01)

(52) U.S. Cl.
CPC ............ *C07C 309/29* (2013.01); *A61P 35/00* (2018.01)

(58) Field of Classification Search
CPC ...... A61K 31/282; C07C 309/29; A61P 35/00
See application file for complete search history.

(56) References Cited

U.S. PATENT DOCUMENTS

2022/0348601 A1* 11/2022 Babak .................. A61P 35/00
2024/0033360 A1* 2/2024 Aboussekhra ......... A61K 45/06

OTHER PUBLICATIONS

L. Li et al., 36 Journal of Chemical Research, 85-89 (2012) (Year: 2012).*
L. Li et al., 81 Bioscience, Biotechnology, and Biochemistry, 1081-1089 (2017) (Year: 2017).*
A. Alsalme et al., 163 Spectrochimica Acta Part A: Molecular and Biomolecular Spectroscopy, 1-7 (2016) (Year: 2016).*
Albukhaty et al., 25 Molecules, 1-13 (2020) (Year: 2020).*
Y. Xue, 18 Expert Opinion on Drug Delivery, 187-203 (2020) (Year: 2020).*
S. Rottenberg et al., 21 Nature Reviews Cancer, 37-50 (2021) (Year: 2021).*
A. Abu-Dief et all., 4 Beni-Suef University Journal of Basic And Applied Sciences, 119-133 (2015) (Year: 2015).*
Alsalme, Ali, et al. "Synthesis, characterization of α-amino acid Schiff base derived Ru/Pt complexes: Induces cytotoxicity in HepG2 cell via protein binding and ROS generation", Spectrochimica Acta Part A: Molecular and Biomolecular Spectroscopy, vol. 163 (Jun. 15, 2016) p. 1-7.
Abu-Dief, Ahmed; Mohamed, Ibrahim M.A. "A review on versatile applications of transition metal complexes incorporating Schiff bases", Beni Suef Univ J Basic Appl Sci. Jun. 2015;4(2):119-133.
Şenocak, Ayşegül, et al. "Novel amino acid Schiff base Zn(II) complexes as new therapeutic approaches in diabetes and Alzheimer's disease: Synthesis, characterization, biological evaluation, and molecular docking studies", Journal of Biochemical and Molecular Toxicology. vol. 36, Iss. 3 (Nov. 23, 2021).
Li, Li-Jun, et al. "Synthesis characterization and cytotoxicity studies of platinum(II) complexes with reduced amino pyridine schiff base and its derivatives as ligands," Bioscience, Biotechnology, and Biochemistry, vol. 81, No. 6, p. 1081-1089.

* cited by examiner

*Primary Examiner* — Alexander R Pagano
(74) *Attorney, Agent, or Firm* — Nath, Goldberg & Meyer; Joshua B. Goldberg

(57) ABSTRACT

A platinum (II) amino acid Schiff base corn, its synthesis, and its use as an anti-cancer or anti-tumor agent.

15 Claims, 2 Drawing Sheets

WATER SOLUBLE PLATINUM (II) AMINO ACID SCHIFF BASE AS AN ANTITUMOR DRUG

BACKGROUND

1. Field

The present disclosure relates to a Pt(II)-complex of an amino acid Schiff base ligand organic chelate ligand, its synthesis and its use as an anti-cancer or anti-tumor agent.

2. Description of the Related Art

There remains an ongoing need for new therapeutically active agents for treating a variety of diseases, disorders, and conditions including, but not limited to, various forms of cancer, various microbial infections, and the like.

The most common cancer diseases for humans are HepG-2 (Hepatocellular carcinoma), HCT-116 (colon carcinoma), and MCF7 (breast adenocarcinoma), which are considered the most dangerous cancers in, for example, the Kingdom of Saudia Arabia.

Currently, chemotherapy, radiation and radiotherapy are represented as the most common treatments against these cancers and for destroying these tumors in the human body without immunotherapy and surgery. Metal organo-framework complexes, involving Rh, Ru, Cu, Pd, Pt, Fe, Os, and Ir, in their organo-complexes have been found to have a high effective potential as anticancer drugs and against tumor growth in the human body. Certain well-known examples include cisplatin, carboplatin, and oxaliplatin of organo-coordinated ligands bonded to $Pt^{2+}$ ion. There are many side effects of cisplatin, carboplatin and, oxaliplatin including cytopenia (involving leukopenia and neutropenia, thrombocytopenia, and anemia), anaphylaxis, ototoxicity, hepatotoxicity, nausea, cardiotoxicity, and vomiting.

The side effects may require patients to be prescribed dose reductions in their platinum drugs during the disease period. Moreover, patients demand extensive follow up of the body biochemistry of the patients, especially the function of kidney and liver due to the effect of the Pt-drug. Finally, patients are commonly co-prescribed additional non-chemotherapy-based drugs to treat the side effects, which can include antiemetics, antibiotics and myeloid growth factors, mannitol, propafenone, saline hyperhydration, magnesium supplements, monoclonal antibody cytokine blockers, and antioxidants.

Therefore, the design of new high soluble and cost-effective, effective, and selective metal organic complexes (MOC) as anticancer drug candidates is an essential demand.

More reactivity for the inhibition of the cancer genesis was established for metal-organic complexes representing the absorption process to the cancer cell walls taking place through a significant distribution progress, which could effectively affect within blocking of the synthesized growth protein, depending on the variation in the lipophilicity, i.e. the Tweedy's chelating theory. Beside the lipophilicity for enhancing the inhibited effect of the metal-organic complexes, the more effective hydrophobic features could also have an obvious role. Referring to the cancer/cancer cell's permeable action, all substances of lipids were convenient for the passage that can be passed through the lipid membrane of the microbe cell. Accordingly, new metal-organic complexes with more progressed features of lipophilicity and hydrophobicity are needed to investigate whether they can easily reduce the cancer metabolism.

Thus, new molecules having desired therapeutic activities and solving the aforementioned problems are desired.

SUMMARY

Presented herein is a novel antitumor drug candidate of a Pt(II)-complex of an amino acid Schiff base ligand organic chelate ligand, herein referred to as PtL. Platinum (II) amino acid Schiff base complex was designed as a water soluble drug candidate fabricated by the coordination of 1 equivalent of an amino acid Schiff base ligand with 1 equivalent of $Pt^{2+}$ ion affording a monometallic PtL complex. Applying alternative analytical spectroscopic techniques was achieved to elucidate the chemical structure of PtL.

The antitumor reactivity of PtL was examined against the growth of three human cancer cell lines (HepG-2 (Hepatocellular carcinoma), HCT-116 (colon carcinoma), and MCF7 (breast adenocarcinoma)), as well as against the human normal cell lines of WI-38. Spectroscopically, the anticancer reactivity of PtL was examined and reported awarding high action against the cancer cell growth. The anticancer reactivities were measured by $IC_{50}$.

In an embodiment, the present subject matter relates to a platinum (II) amino acid Schiff base complex (PtL) having the formula:

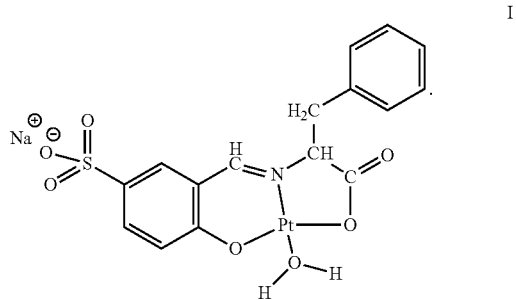

I

In another embodiment, the present subject matter relates to a pharmaceutically acceptable composition comprising a platinum (II) amino acid Schiff base complex as described herein and a pharmaceutically acceptable carrier.

In an additional embodiment, the present subject matter relates to a method of treating cancer or inhibiting tumor growth in a subject comprising administering to a subject in need thereof a therapeutically effective amount of a platinum (II) amino acid Schiff base complex. The cancer or tumor may be one or more selected from the group consisting of hepatocellular carcinoma, colon carcinoma, and breast adenocarcinoma.

In one more embodiment, the present subject matter relates to a method of making the platinum (II) amino acid Schiff base complex as described herein, the method comprising: pouring $H_2L$ in water into platinum chloride in water to form a complexation reaction mixture; stirring the complexation reaction mixture; heating the complexation reaction mixture; removing the water from the complexation reaction mixture; purifying a crude solid through recrystallization to obtain a pure complex; washing the pure complex; and obtaining the platinum (II) amino acid Schiff base complex.

These and other features of the present subject matter will become readily apparent upon further review of the following specification.

DETAILED DESCRIPTION OF THE PREFERRED EMBODIMENTS

Figure 1:
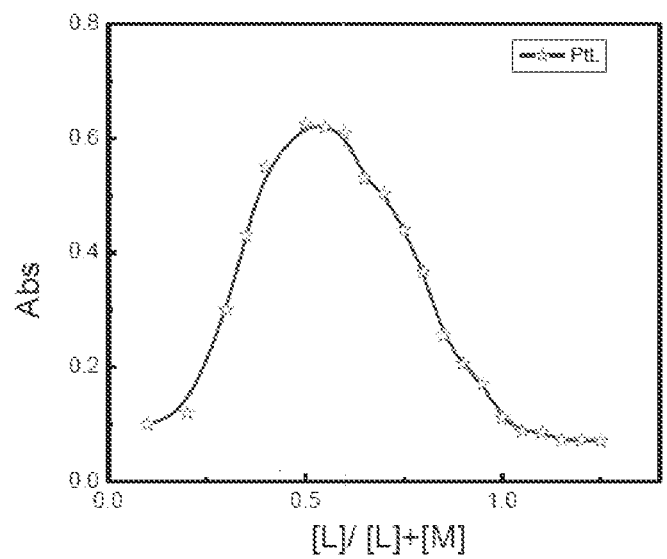
FIG. 1 shows a continuous variation plot for the stoichiometric molar ratios for PtL formed from the $H_2L$ reaction with $Pt^{2+}$ ion with [L] and [M]=$1 \times 10^{-5}$ mol $dm^{-3}$ and 25° C.

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

It will be understood by those skilled in the art with respect to any chemical group containing one or more substituents that such groups are not intended to introduce any substitution or substitution patterns that are sterically impractical and/or physically non-feasible.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

"Subject" as used herein refers to any animal classified as a mammal, including humans, domestic and farm animals, and zoo, sports, and pet companion animals such as household pets and other domesticated animals such as, but not limited to, cattle, sheep, ferrets, swine, horses, poultry, rabbits, goats, dogs, cats and the like.

"Patient" as used herein refers to a subject in need of treatment of a condition, disorder, or disease, such as inhibiting certain enzyme activity and/or treating cancer and tumor activity.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

Presented herein is a novel antitumor drug candidate of a Pt(II)-complex of an amino acid Schiff base ligand organic chelate ligand, herein referred to as PtL. Platinum (II) amino acid Schiff base complex was designed as a water soluble drug candidate fabricated by the coordination of 1 equivalent of an amino acid Schiff base ligand with 1 equivalent of $Pt^{2+}$ ion affording a monometallic PtL complex. Applying alternative analytical spectroscopic techniques was achieved to elucidate the chemical structure of PtL.

The antitumor reactivity of PtL was examined against the growth of three human cancer cell lines (HepG-2 (Hepatocellular carcinoma), HCT-116 (colon carcinoma), and MCF7 (breast adenocarcinoma)), as well as against the human normal cell lines of WI-38. Spectroscopically, the anticancer reactivity of PtL was examined and reported awarding high action against the cancer cell growth. The anticancer reactivities were measured by $IC_{50}$.

In an embodiment, the present subject matter relates to a platinum (II) amino acid Schiff base complex (PtL) having the formula I:

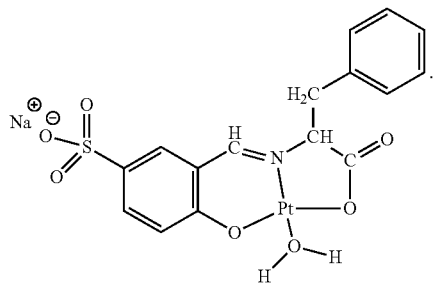

I

In another embodiment, the present subject matter relates to a pharmaceutically acceptable composition comprising a therapeutically effective amount of a platinum (II) amino acid Schiff base complex and a pharmaceutically acceptable carrier.

In still another embodiment, the present subject matter relates to a method of treating cancer in a patient comprising administering to a patient in need thereof a therapeutically effective amount of a platinum (II) amino acid Schiff base complex. The cancer may be selected from the group consisting of hepatocellular carcinoma, colon carcinoma, breast adenocarcinoma, and a combination thereof.

In yet another embodiment, the present subject matter relates to a method of inhibiting tumor activity in a patient comprising administering to a patient in need thereof a therapeutically effective amount of a platinum (II) amino acid Schiff base complex. The tumor may be of a cancer selected from the group consisting of hepatocellular carcinoma, colon carcinoma, breast adenocarcinoma, and a combination thereof.

In this regard, the present subject matter is further directed to pharmaceutical compositions comprising a therapeutically effective amount of a compound as described herein together with one or more pharmaceutically acceptable carriers, excipients, or vehicles. In some embodiments, the present compositions can be used for combination therapy, where other therapeutic and/or prophylactic ingredients can be included therein. In other embodiments, the present compositions can include more than one of the present compounds.

The present subject matter further relates to a pharmaceutical composition, which comprises a present compound together with at least one pharmaceutically acceptable auxiliary.

Non-limiting examples of suitable excipients, carriers, or vehicles useful herein include liquids such as water, saline, glycerol, polyethylene glycol, hyaluronic acid, ethanol, and the like. Suitable excipients for nonliquid formulations are also known to those of skill in the art. A thorough discussion of pharmaceutically acceptable excipients and salts useful herein is available in Remington's Pharmaceutical Sciences, 18th Edition. Easton, Pa., Mack Publishing Company, 1990, the entire contents of which are incorporated by reference herein.

The present compound is typically administered at a therapeutically or pharmaceutically effective dosage, e.g., a dosage sufficient to inhibit enzyme activity and/or treat cancer. Administration of the compound or pharmaceutical compositions thereof can be by any method that delivers the compound systemically and/or locally. These methods include oral routes, parenteral routes, intraduodenal routes, and the like.

While human dosage levels have yet to be optimized for the present compound, generally, a daily dose is from about 0.01 to 10.0 mg/kg of body weight, for example about 0.1 to 5.0 mg/kg of body weight. The precise effective amount will vary from subject to subject and will depend upon the species, age, the subject's size and health, the nature and extent of the condition being treated, recommendations of the treating physician, and the therapeutics or combination of therapeutics selected for administration. The subject may be administered as many doses as is required to reduce and/or alleviate the signs, symptoms, or causes of the disease or disorder in question, or bring about any other desired alteration of a biological system.

In employing the present compound for inhibiting an enzyme activity and/or treating cancer, any pharmaceutically acceptable mode of administration can be used with other pharmaceutically acceptable excipients, including solid, semi-solid, liquid or aerosol dosage forms, such as, for example, tablets, capsules, powders, liquids, suspensions, suppositories, aerosols, or the like. The present compounds can also be administered in sustained or controlled release dosage forms, including depot injections, osmotic pumps, pills, transdermal (including electrotransport) patches, and the like, for the prolonged administration of the compound at a predetermined rate, preferably in unit dosage forms suitable for single administration of precise dosages.

The present compounds may also be administered as compositions prepared as foods for humans or animals, including medical foods, functional food, special nutrition foods and dietary supplements. A "medical food" is a product prescribed by a physician that is intended for the specific dietary management of a disorder or health condition for which distinctive nutritional requirements exist and may include formulations fed through a feeding tube (referred to as enteral administration or gavage administration).

A "dietary supplement" shall mean a product that is intended to supplement the human diet and may be provided in the form of a pill, capsule, tablet, or like formulation. By way of non-limiting example, a dietary supplement may include one or more of the following dietary ingredients: vitamins, minerals, herbs, botanicals, amino acids, and dietary substances intended to supplement the diet by increasing total dietary intake, or a concentrate, metabolite, constituent, extract, or combinations of these ingredients, not intended as a conventional food or as the sole item of a meal or diet. Dietary supplements may also be incorporated into foodstuffs, such as functional foods designed to promote control of glucose levels. A "functional food" is an ordinary food that has one or more components or ingredients incorporated into it to give a specific medical or physiological benefit, other than a purely nutritional effect. "Special nutrition food" means ingredients designed for a particular diet related to conditions or to support treatment of nutritional deficiencies.

Generally, depending on the intended mode of administration, the pharmaceutically acceptable composition will contain about 0.1% to 90%, for example about 0.5% to 50%, by weight of the present compound, the remainder being suitable pharmaceutical excipients, carriers, etc.

One manner of administration for the conditions detailed above is oral, using a convenient daily dosage regimen which can be adjusted according to the degree of affliction. For such oral administration, a pharmaceutically acceptable, non-toxic composition is formed by the incorporation of any of the normally employed excipients, such as, for example, mannitol, lactose, starch, magnesium stearate, sodium saccharine, talcum, cellulose, sodium croscarmellose, glucose, gelatin, sucrose, magnesium carbonate, and the like. Such compositions take the form of solutions, suspensions, tablets, dispersible tablets, pills, capsules, powders, sustained release formulations and the like.

The present compositions may take the form of a pill or tablet and thus the composition may contain, along with the active ingredient, a diluent such as lactose, sucrose, dicalcium phosphate, or the like; a lubricant such as magnesium stearate or the like; and a binder such as starch, gum acacia, polyvinyl pyrrolidine, gelatin, cellulose, and derivatives thereof, and the like.

Liquid pharmaceutically administrable compositions can, for example, be prepared by dissolving, dispersing, etc. an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, for example, sodium acetate, sodium citrate, cyclodextrin derivatives, sorbitan monolaurate, triethanolamine acetate, triethanolamine oleate, etc.

For oral administration, a pharmaceutically acceptable non-toxic composition may be formed by the incorporation of any normally employed excipients, such as, for example, pharmaceutical grades of mannitol, lactose, starch, magnesium stearate, talcum, cellulose derivatives, sodium croscarmellose, glucose, sucrose, magnesium carbonate, sodium saccharin, talcum, and the like. Such compositions take the form of solutions, suspensions, tablets, capsules, powders, sustained release formulations and the like.

For a solid dosage form, a solution or suspension in, for example, propylene carbonate, vegetable oils or triglycerides, may be encapsulated in a gelatin capsule. Such diester solutions, and the preparation and encapsulation thereof, are disclosed in U.S. Pat. Nos. 4,328,245; 4,409,239; and 4,410,545, the contents of each of which are incorporated herein by reference. For a liquid dosage form, the solution, e.g., in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and the like, and encapsulating these solutions or suspensions in hard or soft gelatin capsule shells.

Other useful formulations include those set forth in U.S. Pat. Nos. Re. 28,819 and 4,358,603, the contents of each of which are hereby incorporated by reference.

Another manner of administration is parenteral administration, generally characterized by injection, either subcutaneously, intramuscularly, or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents, solubility enhancers, and the like, such as for example, sodium acetate, sorbitan monolaurate, triethanolamine oleate, cyclodextrins, etc.

Another approach for parenteral administration employs the implantation of a slow-release or sustained-release system, such that a constant level of dosage is maintained. The percentage of active compound contained in such parenteral compositions is highly dependent on the specific nature thereof, as well as the activity of the compound and the needs of the subject. However, percentages of active ingredient of 0.01% to 10% in solution are employable and will be higher if the composition is a solid which will be subsequently diluted to the above percentages. The composition may comprise 0.2% to 2% of the active agent in solution.

Nasal solutions of the active compound alone or in combination with other pharmaceutically acceptable excipients can also be administered.

Formulations of the active compound or a salt may also be administered to the respiratory tract as an aerosol or solution for a nebulizer, or as a microfine powder for insufflation, alone or in combination with an inert carrier such as lactose. In such a case, the particles of the formulation have diameters of less than 50 microns, for example less than 10 microns.

In one embodiment, an amino acid Schiff base ligand ($H_2L$) can be used as starting blocks for the synthesis of the platinum (II) aminoacid Schiff base complex. The preparation of the amino acid Schiff base ligand ($H_2L$) can begin with condensation of sodium sulfonated 2-hydroxybenzaldehyde in water to form a corresponding amino acid Schiff base ligand ($H_2L$) according to Scheme 1 below.

Scheme 1

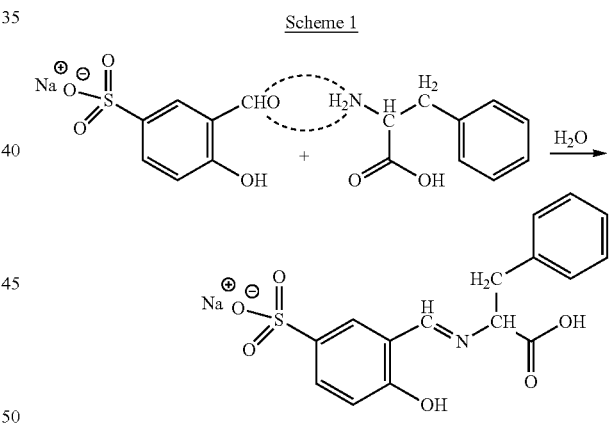

The obtained $H_2L$ is poured into a mixture of platinum chloride and water at room temperature. The mixture is refluxed at about 75° C. to about 85° C., or about 80° C., with magnetic stirring for at least about 3 hours, or about 3 hours. After finishing the complexation reaction, the water (the solvent, water, $H_2O$) is evacuated and the collected target PtL complex is purified through recrystallization using followed by washing.

In one more embodiment, the present subject matter relates to a method of making the platinum (II) amino acid Schiff base complex as described herein, the method comprising: pouring $H_2L$ in water into platinum chloride in water to form a complexation reaction mixture; stirring the complexation reaction mixture; heating the complexation reaction mixture; removing the water from the complexation reaction mixture; purifying a crude solid through recrystallization to obtain a pure complex; washing the pure complex; and obtaining the platinum (II) amino acid Schiff base complex.

The present production methods can be further seen by referring to the following Scheme 2:

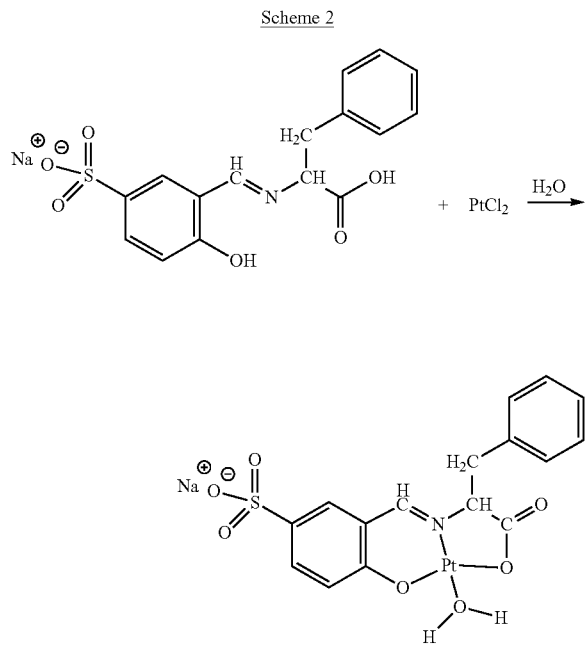

Scheme 2

In an embodiment of the present production methods, the pouring $H_2L$ in water into platinum chloride in water to form a complexation reaction mixture can be conducted at room temperature.

In another embodiment, the stirring may be magnetic stirring.

In still another embodiment, the complexation reaction mixture may be heated to about 80° C.

In further embodiments, the complexation reaction mixture may be heated for about 3 hours.

In another embodiment, the water may be removed through evacuation.

In still another embodiment, the crude solid may be purified using ethanol.

In a further embodiment, the pure complex may be washed with n-hexane.

In another embodiment, the $H_2L$ and platinum chloride may be added in a 1:1 molar ratio.

In other embodiments, the platinum (II) amino acid Schiff base complex or chelate can be obtained in about a 79% yield.

In a further embodiment, the platinum (II) amino acid Schiff base complex may have a melting point of about 300° C. or greater.

The following examples relate to various methods of manufacturing the specific compounds and application of the same, as described herein. All compound numbers expressed herein are with reference to the synthetic pathway figures shown above.

EXAMPLES

Example 1

Preparation of Amino Acid Schiff Base Ligand ($H_2L$)

Condensation of phenyl alanine with sodium sulfonated 2-hydroxybenzaldehyde in water gave of pure $H_2L$.

Example 2

Synthesis of Platinum (II) Amino Acid Schiff Base Chelate

The synthesis begins by gently pouring $H_2L$ (2.0 mmol as 0.74 g in water 30.0 mL) into 0.053 g of platinum chloride (2.0 mmol) in water (30.0 mL) at room temperature. The reaction of complexation was carried out under stirring (magnetically) and heating (at 80° C.) for approximately 3 h. After completion of the complexation reaction, the solvent (water) was removed through evacuation. The remaining impure solid was the target PtL complex. The complex was purified by the recrystallizing process using ethanol followed by washing the pure complex by n-hexane.

The reaction yielded 79% at 0.92 g (as 79%) with a melting point of =>300° C. according to Scheme 2 above.

$^1$HNMR spectra of PtL: δ=10.32 (s, 1H, CH=N), 8.87 (s, 1H), 7.93 (s, 2H), 7.70 (s, 1H), 7.03 (s, 1H), 6.96 (s, 2H), 5.98 (s, 1H, CH-aliphatic), 3.82 (s, 2H, $CH_2$-aliphatic) and 2.51 ppm (s, 2H, $H_2O$), $^{13}$CNMR spectra of PtL: δ=181.78 (CH, CH=N), 172.81 ($C_q$, C=O), 153.42 ($C_q$, C—O), 139.26 ($C_q$), 136.87 (J=82 Hz, CH), 134.71 ($C_q$), 129.59 (CH), 128.84 (CH), 127.44 (CH), 126.73 (CH), 126.42 ($C_q$), 124.93 (CH), 123.94 (CH), 120.40 (CH), 93.74 (CH) and 64.08 ppm ($CH_2$), The organo-ligand was obtained from the condensed combination reaction of phenyl alanine with sodium sulfonated 2-hydroxybenzaldehyde in water (Scheme 1, above). For an aqueous solution of one equivalent of $Pt^{II}$ ion of platinum chloride, the complexation was accomplished, as shown in Scheme 2, above. The structure of PtL was examined with all available spectroscopic tools, NMR, infrared and ultraviolet-visible spectra. Moreover, the current compounds were examined by the elemental composition analyses (EA), which are represented in Table 1.

TABLE 1

| CHN percentage analyses and UV Vis. spectrum of $1.0 \times 10^{-5}$ mol · $dm^{-3}$ solutions in DMF at 25° C. for PtL | | | | | | | |
|---|---|---|---|---|---|---|---|
| | | | | | | Electronic spectra | |
| Comp. | | CHN analyses, % | | | $\lambda_{max}$, | ε, $mol^{-1}$, | |
| (M. W.) | Color | C | H | N | nm | $cm^{-1}$ | Assign. |
| PtL (582.42 g · $mol^{-1}$) | Pale brown | 32.78 (33.00) | 2.57 (2.42) | 2.35 (2.40) | 245 314 389 | 10104 4256 3520 | π→π* /n→π* L-MCT |

The percentage ratios of carbon, hydrogen and nitrogen (main component elements) in PtL were estimated and determined to assign the degree of their purity, as listed in Table 1. They were matched with the calculated ones for their tentative composition (with lower differentiation than 0.4%, as observed Scheme 2).

Further, the measured melting point for the solid of PtL was found as >300° C., appropriating the observed stability of PdL chelate. In DMSO, the molar ratios of $Pt^{2+}$ ion to organo-ligand (amino acid Schiff base) molecule to give PtL complex (the stoichiometry) was examined using continuous variation methods.

Figure 2:
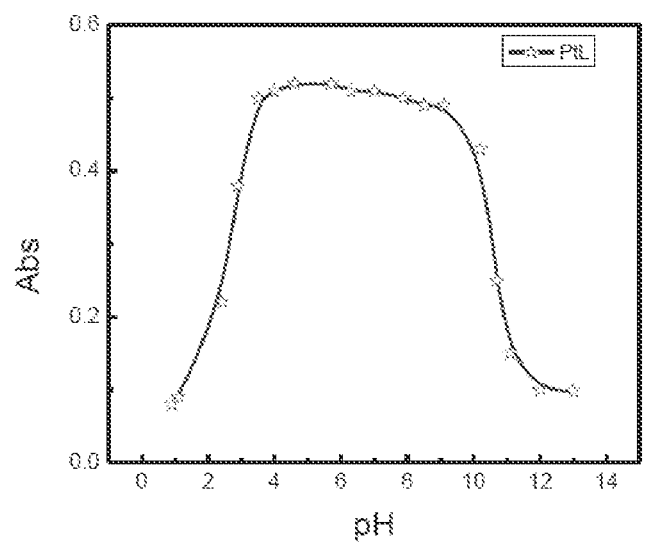
FIG. 2 shows the pH effect stability of an aqueous solution of the PtL complex.

From FIG. 1, the results assigned that PtL chelate was synthesized by a coordination of amino acid Schiff base ligands with $Pt^{2+}$ ions in 1:1 molar ratios (Scheme 2). From FIG. 2, the pH stability detection for an aqueous solution of PtL in various pH values using standard universal buffer solutions, was examined. PtL chelate exhibited a wide range of pH stability 3.5-10.5.

Example 4

Electronic Spectroscopy

Figure 3:
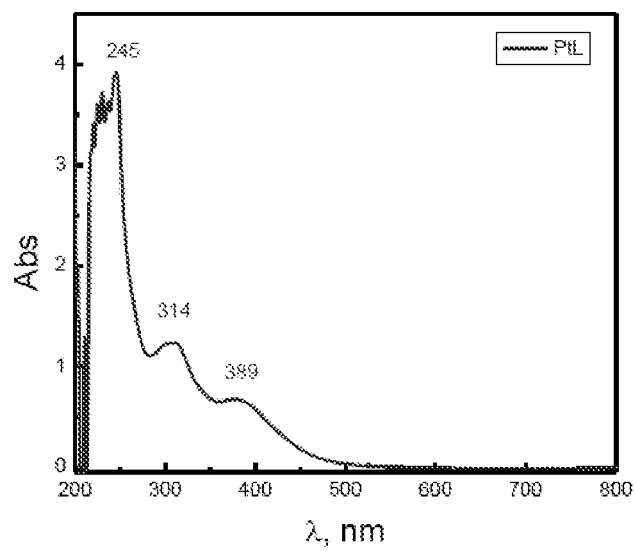
FIG. 3 shows the UV-Vis. spectrometric scans for concentrations=$1.0 \times 10^{-6}$ mol $dm^{-3}$ of PtL in an aqueous media at 25° C.

The concentration of PtL in water=$1.0 \times 10^{-6}$ mol $dm^{-3}$ at 25° C., Table 1 and shown in FIG. 3, represent all possible electronic transitions. All $\lambda_{max}$=wavelengths for the optimized absorbed transitions, and the corresponded ε=molar absorptivities.

Example 5

FT-IR Spectra

Figure 4:
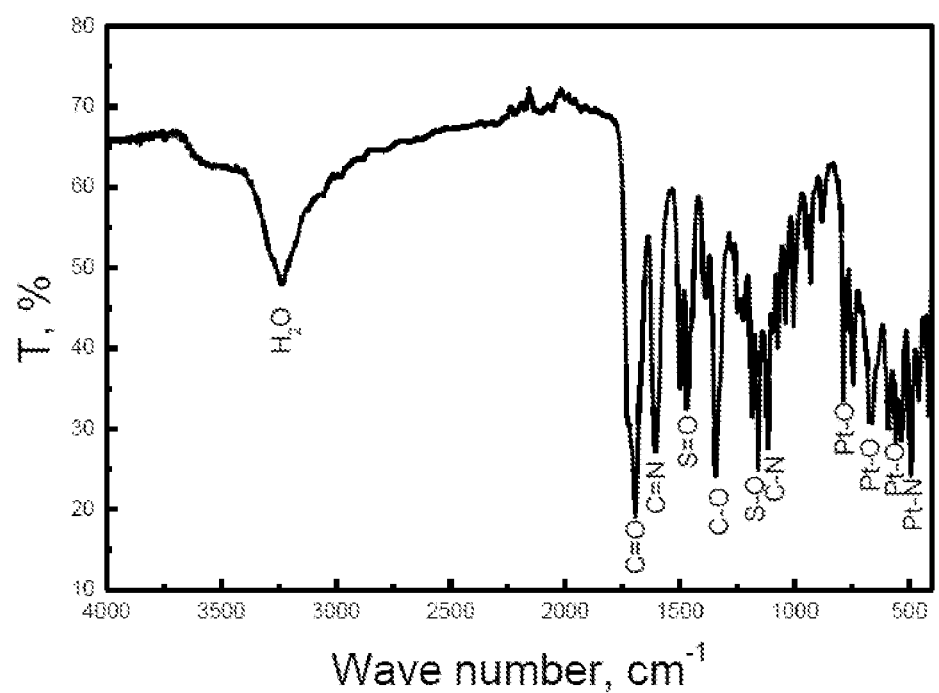
FIG. 4 shows FT-IR spectra of PtL at 25° C.

The FT-IR absorption spectroscopy for the molecules of PtL at 25° C. were studied and recorded in FIG. 4.

Example 6

Anticancer Assays

Investigation for the bio-reactivity of PtL, as an antitumor candidate, was achieved versus well documented human cancer cell lines, as three cancers entitled HepG2, MCF-7, and HCT-116, using the simplest tool SRB (sulforhodamine-B-stain). In particular, the most popular anticancer referenced drug (vinblastine) was used in the anticancer assay (the inhibited action of the cancer cells) to compare its bio-reactivity versus that one of PtL. The antitumor reactivity of PtL was evaluated by $IC_{50}$ concentrations (half effected concentration in μM) for inhibiting the growth of the tumor and normal cell lines of human in which $IC_{50}$ concentrations were obtained from Eq. 1, below.

With HepG-2 (Hepatocellular carcinoma), HCT-116 (colon carcinoma), and MCF7 (breast adenocarcinoma), as human cancer cell lines, the antitumor potential of PtL was studied against their growth by applying a spectrometric tool. Using SRB (sulforhodamine-B-stain) was essential in the spectrometric studies at a specific wavelength (564 nm, the optimized absorption wavelength). Recording the corresponded absorbance (A) at 564 nm was accomplished using a UV/Vis. spectrophotometer, UV-1800 mode Shimadzu with a mono-cell holder. With plates of 96-multiwell model, the culture of the current human cancer cell lines of $10^4$ cells per well were accomplished followed by a gentle addition of DMSO solution of $H_2L$ or PdL the cultured wells of the cancer cell lines.

The resulting mixed solution of PtL solution with the subjected cancer cell line of human in SRB was assigned in incubated isolated atmosphere for 48 hours at 37° C. The isolated atmosphere was accomplished by $CO_2$ gas bubbling with v/v 15%.

The same procedure was followed with vinblastine, as vinblastine was subjected as a reference anticancer agent to compare its reactivity against that one of the studied PtL. For WI-38, as the normal human fetal lung fibroblast, the pervious procedure of the cancer cell lines was applied for $H_2L$ and PdL to evaluate their selectivity index. Using Eq. 1, below, to derive the inhibited potential of PtL against the growth of the human cancer and normal cell lines through their effective concentration in μM ($IC_{50}$, the half effective concentration of PtL):

$$IC_{50}(\mu M) = \frac{Control_{OD} - Compound_{OD}}{Control_{OD}} \times 100 \qquad \text{Equation (1)}$$

Free DMSO was subjected as the standard applied solvent, i.e. the negative reference for determining the valuable inhibited potential of the current PtL reagent for the normal/cancer cell lines of human growth.

Notably, the $IC_{50}$ concentrations were diminished with PtL by 32.14 μM against the growth of HCT-116, 23.09 μM against the growth of MCF-7, and finally 22.15 μM against the growth of HepG-2, respectively. Hence, the antitumor study assigned the influence of the central metal ion within the Tweedy's chelation effect on the bio-action of $Pt^{2+}$ ion in PtL.

TABLE 2

$IC_{50}$, The anticancer index of PtL versus the titled cancer/normal cell lines of human.

| | $IC_{50}$ (μM) | | | | Selectivity index | | |
|---|---|---|---|---|---|---|---|
| Comp. | HCT-116 | MCF-7 | HepG-2 | WI-38 | HCT-116 | MCF-7 | HepG-2 |
| PtL | 32.14 ± 20.60 | 23.09 ± 0.25 | 22.15 ± 0.72 | 111.21 ± 0.62 | 3.47 | 4.83 | 5.05 |
| Vinblastine | 13.30 ± 0.11 | 4.12 ± 0.14 | 7.50 ± 0.10 | — | — | — | — |

The Lewis acidity and lipophilic features of PtL may enhance the anticancer effectiveness. The bio-action was established with the presence of $Pt^{2+}$ ions in PtL complex based on the chelator effect (Tweedy theory).

The index of selectivity percentages, as listed in Table 2 for comparing results for the cancer (HepG2, MCF-7 and HCT-116) and normal (WI-38) cell lines for PtL were derived. PtL reported more progressed selectivity index, assigning the distinguished action of $Pt^{2+}$. Consequently, the less toxic effect of PtL against the growth of WI-38 could represent PtL as a noble candidate for the chemotherapy for various cancer cell lines. PtL complex could be safe for the normal human cells population.

It is to be understood that the platinum (II) amino acid Schiff base complex (PtL), compositions containing the same, and methods of using and producing the same are not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A platinum (II) amino acid Schiff base complex having the formula:

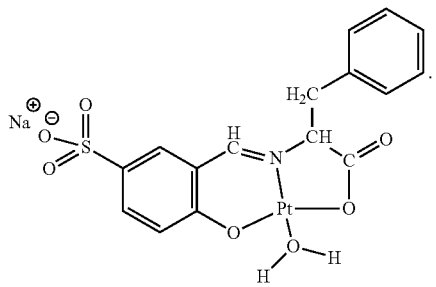

2. The platinum (II) amino acid Schiff base complex of claim 1, wherein the platinum (II) amino acid Schiff base complex has a melting point of greater than 300° C.

3. A pharmaceutically acceptable composition comprising a therapeutically effective amount of the platinum (II) amino acid Schiff base complex of claim 1 and a pharmaceutically acceptable carrier.

4. A method of treating cancer in a patient comprising administering to a subject in need thereof a therapeutically effective amount of the platinum (II) amino acid Schiff base complex of claim 1.

5. The method of treating cancer of claim 4, wherein the cancer is one or more selected from the group consisting of hepatocellular carcinoma, colon carcinoma, and breast adenocarcinoma.

6. The method of treating cancer of claim 5, wherein the cancer is hepatocellular carcinoma, colon carcinoma, or breast adenocarcinoma.

7. A method of making the platinum (II) amino acid Schiff base complex of claim 1, the method comprising:
    pouring $H_2L$ in water into platinum chloride in water to form a complexation reaction mixture;
    stirring the complexation reaction mixture;
    heating the complexation reaction mixture;
    removing the water from the complexation reaction mixture;
    purifying a crude solid through recrystallization to obtain a pure complex;
    washing the pure complex; and
    obtaining the platinum (II) amino acid Schiff base complex.

8. The method of making the platinum (II) amino acid Schiff base complex of claim 7, wherein the stirring is magnetic stirring.

9. The method of making the platinum (II) amino acid Schiff base complex of claim 7, wherein the complexation reaction mixture is heated to about 80° C.

10. The method of making the platinum (II) amino acid Schiff base complex of claim 7, wherein the complexation reaction mixture is heated for about 3 hours.

11. The method of making the platinum (II) amino acid Schiff base complex of claim 7, wherein the water is removed through evacuation.

12. The method of making the platinum (II) amino acid Schiff base complex of claim 7, wherein the crude solid is recrystallized from ethanol.

13. The method of making the platinum (II) amino acid Schiff base complex of claim 7, wherein the pure complex is washed with n-hexane.

14. The method of making the platinum (II) amino acid Schiff base complex of claim 7, wherein $H_2L$ and platinum chloride are added in a 1:1 molar ratio.

15. The method of making the platinum (II) amino acid Schiff base complex of claim 7, wherein the platinum (II) amino acid Schiff base complex has a melting point of greater than 300° C.

* * * * *